US005999557A

United States Patent [19]

Molloy et al.

[11] Patent Number: 5,999,557

[45] Date of Patent: Dec. 7, 1999

[54] STEEL MAKING BATH CONTROL

[75] Inventors: Neil Adrian Molloy, Adamstown Heights, Australia; Grant Caffrey, Vancouver, Canada

[73] Assignee: The Broken Hill Proprietary Company, Melbourne, Australia

[21] Appl. No.: 09/100,347

[22] Filed: Jun. 19, 1998

[51] Int. Cl.[6] ........................ A61B 1/04

[52] U.S. Cl. ........................ 373/72; 373/85

[58] Field of Search ........................ 373/72, 2, 85, 373/60; 266/47

[56] References Cited

U.S. PATENT DOCUMENTS

| | | | |
|---|---|---|---|
| 4,730,336 | 3/1988 | Herneisen et al. | 373/2 |
| 4,827,486 | 5/1989 | Brotzmann et al. | 373/2 |
| 5,237,585 | 8/1993 | Stenkvist | 373/72 |
| 5,444,733 | 8/1995 | Coassin et al. | 373/72 |
| 5,635,130 | 6/1997 | Leczo et al. | 266/47 |
| 5,802,097 | 9/1998 | Gensini et al. | 373/72 |

*Primary Examiner*—Philip H. Leung
*Assistant Examiner*—Quang Van
*Attorney, Agent, or Firm*—Kerkam, Stowell, Kondracki & Clarke, P.C.; John C. Kerins

[57] ABSTRACT

This invention is directed to a method and apparatus for thermal homogenization of molten metal in a heath of a electric arc furnace for steel production. The invention addresses the problem of lack of thermal homogenization by providing a lance which directs oxygen gas downwardly towards the surface of the bath and into the molten metal in a direction that diverges away from a direct line to a central region of the hearth through a horizontal divergence angle in the range of 10° to 50° thereby to enhance movement of the molten metal about the hearth and the direction of the gas is inclined downwardly to strike the nominal horizontal plane of the surface of the bath at an inclined angle in the range of 35° to 50° thereby to minimize splashing of the molten metal.

29 Claims, 3 Drawing Sheets

STEEL MAKING BATH CONTROL

BACKGROUND OF THE INVENTION

This invention relates to a method and apparatus for thermal homogenisation of molten metal in a metallurgical vessel and in particular but not exclusively to electric arc furnaces for steel production.

Electric arc furnaces in steel processing are used to melt down ferrous materials and refine them into molten metal before tapping into a ladle. The furnaces usually comprise a hearth of generally crucible shape into which ferrous materials such as, for example, scrap, are charged, one or more electrodes adapted to melt the ferrous material with electric arc heating to form a bath of metal and one or more gas injection ports in the bottom of the hearth through which argon is directed into the molten metal for the purposes of stirring the bath.

To enhance melting of ferrous material and to post combust carbon monoxide within the furnace it has also been proposed to blow oxygen into the hearth from above the level of the bath.

In more recent times, other hearth shapes have been proposed. Such hearths generally comprise a deep portion, referred to hereinafter as a crucible, adapted to hold the bulk of the molten metal, at one end of the hearth and at the other end a shallow portion, hereinafter referred to as a balcony. The balcony is generally provided with a taphole in its base or an outwardly projecting spout in its wall. The one or more electrodes used in the furnace are generally placed within the crucible zone. Typically hearths of this kind are tiltable to facilitate tapping.

Additionally, they are so shaped to enable some molten metal to remain in the crucible at the conclusion of the tilting/tapping operation to avoid slag entrainment when tapping the steel.

A problem that has been observed in electric arc furnaces in general is that the temperature of the molten metal in the hearth is not homogeneous. In particular, “cold spots” and “hot spots” have been observed in the hearth, that is, positions in the hearth at which the temperature of the molten metal is relatively lower and higher respectively than that of the bulk of the molten metal.

It has been observed that this disparity is exacerbated in hearths having balconies and that the temperature of the molten metal in the balcony is relatively lower than that of the molten metal in the crucible. It has also been observed that the temperature of the molten metal towards the walls of the hearth is relatively lower than that of the molten metal towards the centre of the crucible with the exception of the areas near the electrode where the opposite is the case.

It has also been observed in hearths provided with means to blow oxygen into the hearth from above the level of the bath that continued blowing of oxygen after the scrap has melted can produce splashing of molten metal onto the walls of the hearth and back splash onto the oxygen blowing means causing deterioration of the wall surfaces and of the oxygen blowing means respectively.

Continued operation of the scrap melting apparatus after the ferrous materials have been converted to molten metal is often required to heat the molten metal to a predetermined temperature and/or maintain that temperature prior to tapping.

An object of the present invention is to address the above problems of the prior art.

SUMMARY OF THE INVENTION

The present invention provides an electric arc furnace comprising a vessel for holding molten metal;

heating means operable to heat molten metal within the vessel including at least one electrode placed within the vessel;

and gas jet means to direct a jet of combustible gas downwardly into the molten metal in the vessel in a general direction which is inclined downwardly by an angle in the range of 35° to 50° from the horizontal and which diverges away from a direct line to a central region of the vessel through a horizontal divergence angle in the range of 10° to 50°.

Preferably the gas jet means is positioned so as to deliver said jet of gas downwardly towards the surface of the molten metal in the vessel so as to penetrate the surface and extend into the molten metal without substantial splashing.

It is preferred that the jet of gas has a gas flow rate in the supersonic range, and more preferably in the range of 2000 to 3500 Nm3/hr.

The jet of gas may fan outwardly along said general direction of the jet.

Preferably the gas jet means is in the form of an oxygen lance operable to produce said jet of gas as a jet of oxygen from a tip of the lance.

The tip of the lance may be provided with a pair of divergent nozzles to produce an outwardly fanning jet having an included angle in the range of 16° to 47°.

Preferably the heating means comprises three electrodes placed within the crucible zone.

Preferably further the vessel is adapted to hold ferrous materials for melting and refining into said molten metal and the one or more electrodes facilitate melting of said ferrous materials.

The balcony may extend from one side of the crucible thereby forming a hearth having an upper portion of, for example, tear-drop, elliptical or ovoid shape in horizontal cross-section. The crucible may be of generally cup shape.

The invention also provides a method of heating molten metal within a vessel comprising a hearth having a crucible and a balcony, in which the balcony extends from one side of the crucible thereby forming a hearth having an upper portion of any one of tear-drop, elliptical or ovoid shape in horizontal cross-section and the crucible is of generally cup shape and provides a deeper reservoir for the molten metal than the balcony and which includes the step of directing a jet of combustible gas downwardly into the molten metal in the vessel in a general direction which is inclined downwardly by an angle in the range of 35° to 50° from the horizontal and which diverges away from a direct line to a central region of the vessel by a horizontal divergence angle in the range of 10° to 50°.

It is preferred that said horizontal divergence angle is in the range of 30° to 35°.

More preferably said horizontal divergence angle is 31.5°.

It is also preferred that said inclined angle is in the range of 38° to 47°.

The balcony may be provided with a taphole in its bottom, an outwardly projecting spout in its wall or other tapping means.

Preferably the method further comprises the steps of placing ferrous materials into the vessel and melting and refining the ferrous materials to provide said molten metal.

Preferably the method comprises the further step of heating the molten metal to a predetermined temperature prior to tapping.

Preferably said melting and heating steps are provided by electric arc heating.

Preferably further that electric arc heating is provided by three electrodes within the vessel.

Preferably further the vessel is a hearth of an electric arc furnace and the crucible is adapted to hold ferrous materials for melting and refining into said molten metal and the three electrodes facilitate melting of said ferrous materials and heating of the molten metal.

It is preferred that the three electrodes are able to be placed within the crucible zone after the ferrous material is charged thereinto.

It is preferred that the molten metal is tapped through a taphole provided in the bottom of the balcony and that tapping is facilitated by tilting of the vessel. Additionally, it is preferable that the vessel is so shaped to enable some molten metal to remain in the crucible at the conclusion of the tilting/tapping operation to prevent slag entrainment when tapping the steel.

Preferably the jet of combustible gas is oxygen and is delivered by an oxygen lance which is water cooled.

It is preferred that the tip of the lance is disposed above the molten metal.

Preferably further the tip is provided with a pair of divergent nozzles having an acute included angle of about 30°.

Preferably the lance is mounted on a stand at the crucible end of the hearth.

It is preferred that a gas injection port is provided in the crucible bottom proximal to the balcony.

BRIEF DESCRIPTION OF THE DRAWINGS

In order that the invention may be more fully explained one particular embodiment will be described in detail with reference to the accompanying drawings in which.

DESCRIPTION OF THE PREFERRED EMBODIMENT

Figure 1:
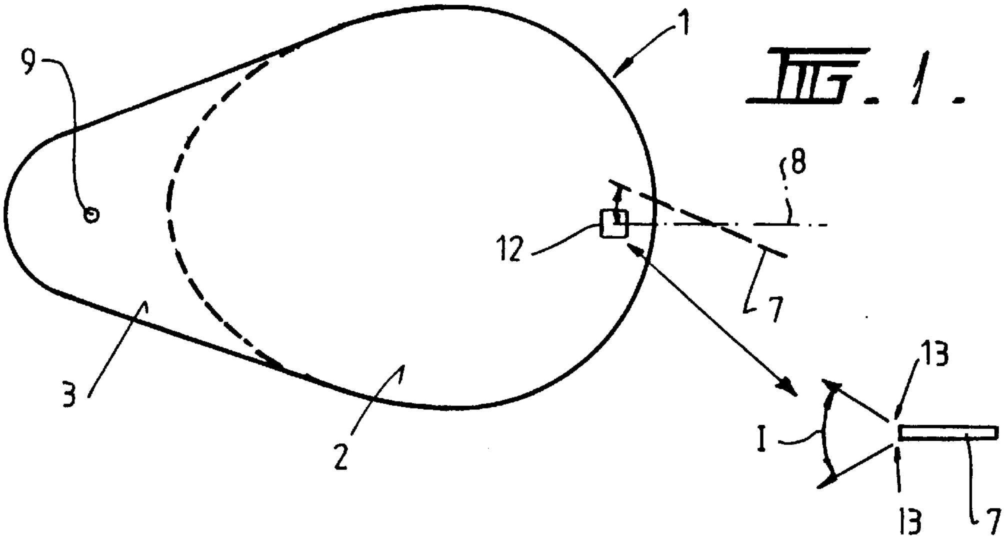
FIG. 1 is a diagrammatic horizontal section of an embodiment of apparatus according to the invention.
Figure 2:
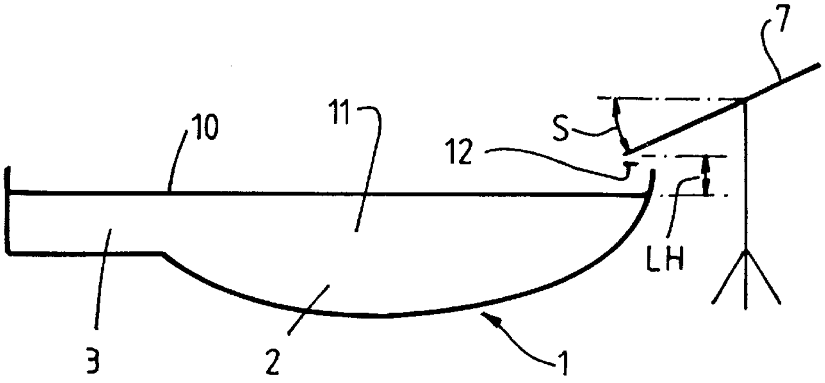
FIG. 2 is diagrammatic vertical section of the embodiment illustrated in FIG. 1.
Figure 3:
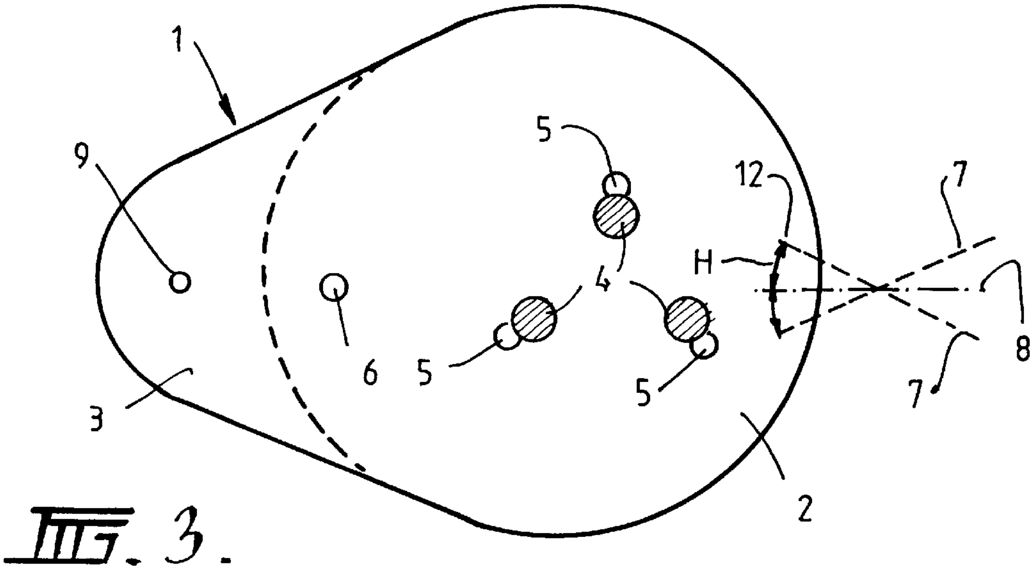
FIG. 3 is a diagrammatic horizontal section similar to that of FIG. 1 illustrating additional detail to that shown in FIG. 1.

A vessel in accordance with an embodiment of the invention comprises a hearth 1 of an electric arc furnace. The hearth 1 as illustrated by FIGS. 1 to 3 comprises a crucible 2 of generally cup shape having a balcony 3 extending from a side wall thereby providing the upper portion of the hearth 1 with a generally teardrop shape in horizontal cross-section. The crucible 2 provides a deeper reservoir 11 for the molten metal than the balcony 3. A typical hearth 1 has a capacity of 40 to 150 tonnes of molten steel.

As best illustrated by FIG. 3, in use three electrodes 4 are disposed in the crucible 2 and three gas injection ports 5 are provided in the bottom of the crucible 2 through which inert gas, air, oxygen or other gas is directed into the crucible 2, with each port 5 disposed substantially below a respective electrode 4.

Additionally oxygen is also blown into the hearth 1 from above by gas jet means in the form of a water cooled oxygen lance 7. In use, the flow rate of the oxygen is generally maintained in the supersonic range, and typically in the range of 2000 to 3500 Nm3/hr. An average flow rate of 2500 Nm3/hr provides acceptable operating conditions in the hearth. The lance 7 is mounted on a stand outside the crucible 2 at a position remote from the balcony 3. The stand lies at a point on the centre line 8 of the hearth 1 with the lance 7 pivotable thereabout. The balcony 3 is provided with a taphole 9 in its bottom and the hearth 1, supported by rockers (not shown), is tiltable to facilitate tapping.

In operation ferrous materials, such as, for example, scrap metal, are charged into the crucible 2, three electrodes 4 adapted to melt the charged scrap with electric arc heat are emplaced into the crucible 2. Three gas injection ports 5 provided in the bottom of the crucible 2 direct inert gas or oxygen into the crucible 2 from below the scrap, with each port 5 disposed substantially below a respective electrode 4. Once the scrap has melted, a reservoir 11 of molten metal is formed within the hearth 1. The reservoir 11 is heated to a prerequisite temperature with the same apparatus that was used to melt the scrap. Additionally oxygen is blown into the hearth 1 from the lance 7 once a molten pool of metal has formed.

An additional port 6 is provided in the bottom of the crucible 2 close to the balcony 3. The provision of this additional port 6 enhances molten metal movement in the balcony 3.

A typical molten metal reservoir 11 is illustrated in FIGS. 1, 2 and 3. The orientation of the oxygen lance 7 with respect to the nominal horizontal plane 10 of the surface of the reservoir 11 and the hearth 1 is illustrated by FIG. 2. FIG. 2 also illustrates the disposition of the tip 12 of the oxygen lance 7 above a nominal horizontal plane 10 of the surface of the molten metal reservoir 11 and the direction in which it directs oxygen downwardly into the molten bath. FIG. 3 illustrates two preferred orientations of the lance at horizontal divergence angles H of +20° and −20°.

In accordance with the invention the lance 7 directs oxygen gas downwardly towards said surface of the reservoir 11 and into the molten metal in a direction that diverges away from a direct line to a central region of the hearth through a horizontal divergence angle H in the range of 10° to 50° thereby to enhance movement of the molten metal about the hearth and the direction of the gas is inclined downwardly to strike the nominal horizontal plane 10 of the surface of the reservoir 11 at an inclined angle S in the range of 35° to 50° thereby to minimise splashing of the molten metal.

Additionally, the balcony 3 and crucible 2 are so shaped to enable some molten metal, typically 5 to 10 tonnes, to remain in the crucible 2 at the conclusion of the tilting/tapping operation to avoid slag entrainment when tapping the steel.

Experimental water modelling suggests that a horizontal divergence angle H in the range of 10° to 50° and an inclined angle S in the range of 35° to 50° would provide effective homogeneity of molten metal temperature in the reservoir 11 and minimise splashing therein. Additionally the results suggest that a horizontal divergence angle H of about 31.5° and an inclined angle S in the range of 38° to 47° would provide more effective homogeneity of molten metal temperature in the reservoir 11 and minimise splashing therein than other orientations.

Experimental water modelling was conducted on a ⅓ scale model of a hearth 1 with nitrogen gas and water simulating the interaction of oxygen and steel in these experiments. Experimental results are illustrated by FIGS. 4 to 5 inclusive.

Figure 4:
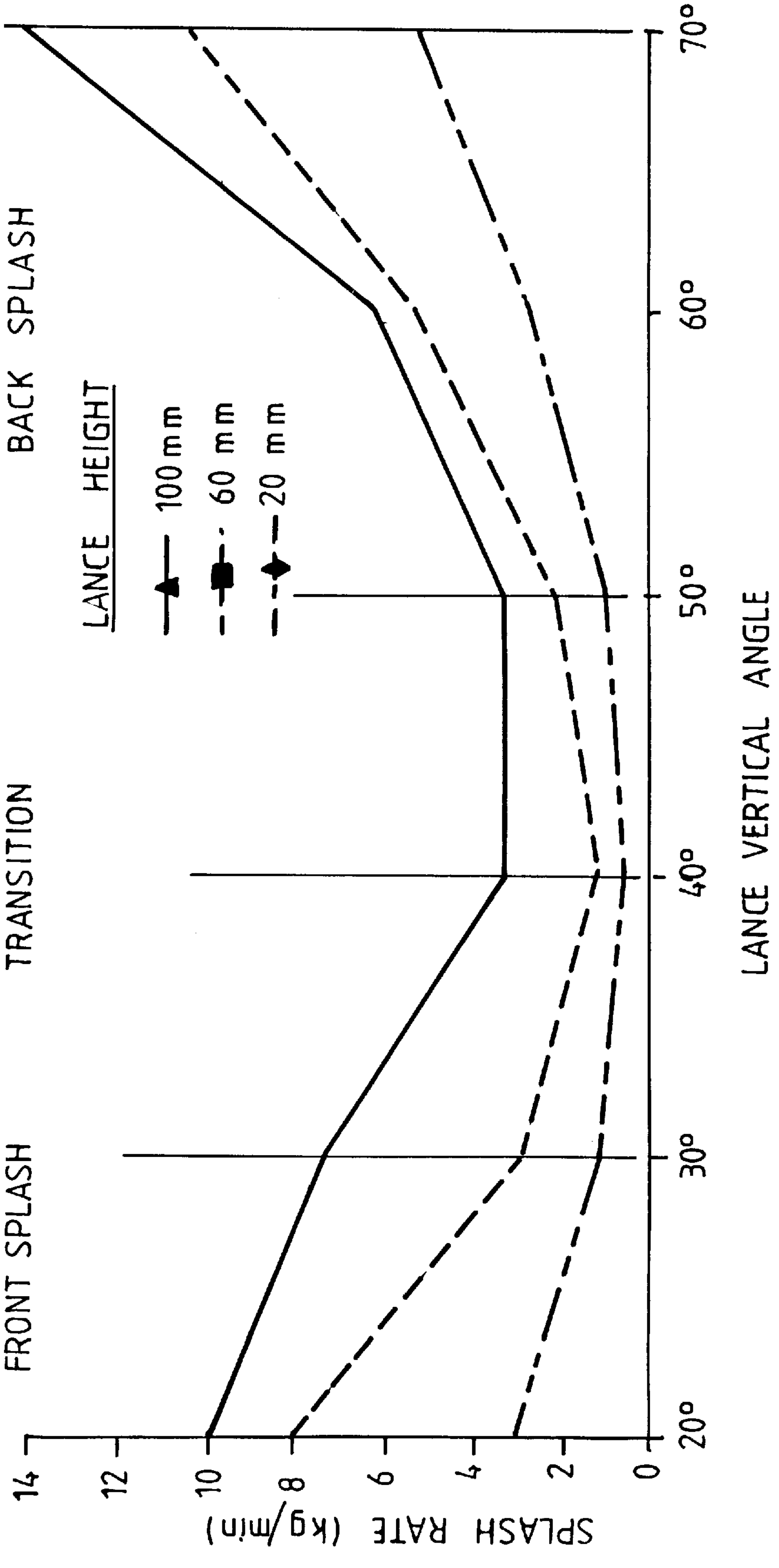
FIG. 4 is a graph of test results based on water modelling experiments on apparatus according to the invention.

FIG. 4 is a graph which illustrates experimental water modelling results plotting splash rate against six distinct inclined angles S (20°, 30°, 40°, 50°, 60°, and 70°) for each of three lance heights LH (20 mm, 60 mm and 100 mm). The methodology of the water modelling tests for splash generation was to measure splash by running the model for 10 minutes and recording the change in the volume of the reservoir 11. The graph illustrates that inclined angles S in the range of 30° to 50° provided for minimal splash whereas changes in lance tip height LH have minimal effect.

Figure 5:
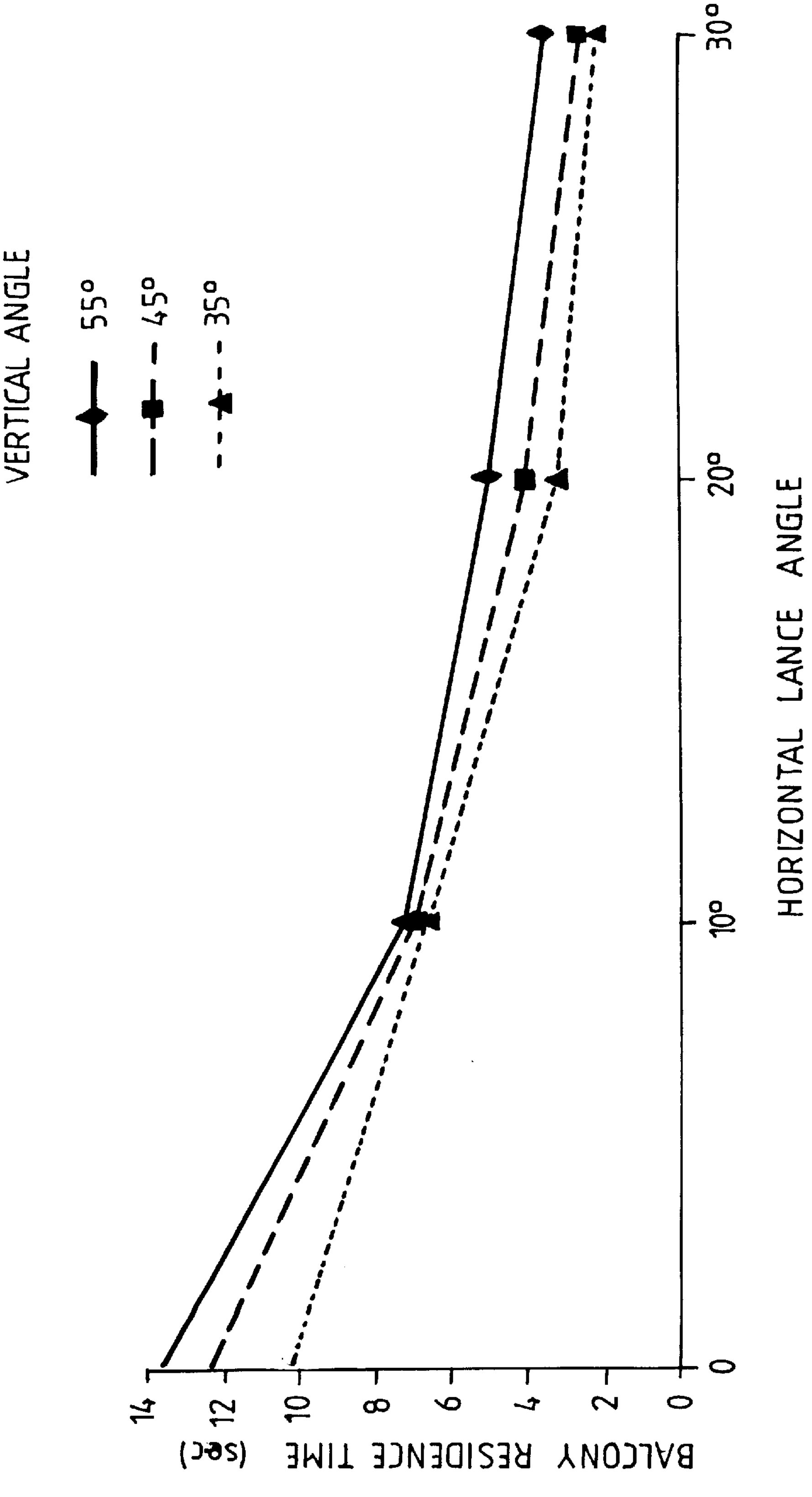
FIG. 5 is a graph of test results based on water modelling experiments on apparatus according to the invention.

FIG. 5 is a graph which illustrates experimental water modelling results plotting balcony 3 residence time of tracer particles in the model as a measure of molten metal motion against four distinct lance horizontal divergence angles H (0°, 10°, 20° and 40°) for each of three inclined angles S (55°, 45° and 35°). The particles were placed on the surface 11 of the molten metal directly above the taphole 9 and the time for them to exit the balcony 3 were recorded. The graph illustrates (1) that if the lance 7 is directed along the hearth 1 centre line 8 there is little motion in the balcony 3 resulting in the formation of a cold zone; (2) that offsetting the horizontal angle from the centre line 8 of the hearth 1 can substantially and significantly reduce balcony 3 residence time and hence improve temperature homogenisation and (3) that changes in inclined angle S in the range of 35° to 55° have minimal effect.

It has also been found that the tip 12 of the lance 7 should be held above and close to the bath to enhance efficiency particularly during flat surface conditions, viz FIG. 4.

This modelling has established that it is possible to enhance and take advantage of the natural "gulf streaming" effect while utilising existing geometry and apparatus in the electric arc furnace, as well as increase the associated roll over in the bath to counter stratification caused by idiosyncrasies of the furnace geometry.

In accordance with an embodiment of the invention the tip 12 is provided with a pair of divergent nozzles 13 having an acute included angle I, preferably of 30° as indicated in scrap detail in FIG. 1.

A method according to an embodiment of the invention comprises the steps of placing ferrous materials, such as scrap, into the hearth 1 of an electric arc furnace and melting the scrap metal to provide molten metal, holding the molten metal as a reservoir 11 in said hearth 1, heating said molten metal to a predetermined temperature by electric arc heat, directing a jet of gas downwardly into a nominal horizontal plane 10 of the surface of said molten metal to strike said surface at an inclined angle S in the range of 35° to 50° preferably 40° to 45° thereby to minimise splashing of the molten metal and offsetting the direction of the jet of gas from a central vertical axis of the vessel by a horizontal divergence angle H in the range of 10° to 50° preferably 31.5° thereby to enhance movement of the molten metal about said axis. Once the requisite temperature of the molten metal has been reached the molten metal is tapped through a taphole 9 provided in the bottom of the hearth 1 and said tapping is facilitated by tilting of the hearth 1.

The three electrodes 4 provide the heating means to melt the scrap metal into said molten metal and to raise the temperature of the molten metal to its predetermined temperature.

Accordingly, the present invention provides a method and apparatus that improves temperature homogenisation within molten metal held in a metallurgical vessel.

The method and apparatus of the present invention enhances flow and heat transfer of the molten metal in the vessel to minimise cold and hot spots in the molten metal in particular addresses the problem of thermal homogeneity in the balcony of an electric arc furnace.

A particular embodiment of the invention has been described and illustrated by way of example, but it will be appreciated that other variations of and modifications to the invention can take place without departing from the spirit and scope of the invention.

We claim:

1. An electric arc furnace comprising a vessel for holding molten metal;

heating means operable to heat molten metal within the vessel including at least one electrode placed within the vessel;

and at least one oxygen lance operable to direct a jet of oxygen downwardly into the molten metal in the vessel in a general direction which is inclined downwardly by an angle in the range of 35° to 50° from the horizontal and which diverges away from a direct line to a central region of the vessel through a horizontal divergence angle in the range of 10° to 50°.

2. An electric arc furnace according to claim 1 wherein the jet of oxygen has a gas flow rate in the supersonic range.

3. An electric arc furnace comprising a vessel for holding molten metal;

heating means operable to heat molten metal within the vessel including at least one electrode placed within the vessel;

and at least one oxygen lance operable to direct a jet of oxygen downwardly into the molten metal in the vessel in a general direction which is inclined downwardly by an angle in the range of 35° to 50° from the horizontal and which diverges away from a direct line to a central region of the vessel through a horizontal divergence angle in the range of 10° to 50°, and wherein the jet of oxygen has a gas flow rate in the range of 2000 to 3500 $Nm^3$/hr.

4. An electric arc furnace according to claim 3 wherein the at least one oxygen lance is positioned so as to deliver said jet of oxygen downwardly towards the surface of the molten metal in the vessel so as to penetrate the surface and extend into the molten metal without substantial splashing.

5. An electric arc furnace according to claim 3 wherein the jet of oxygen fans outwardly along said general direction of the jet.

6. An electric arc furnace according to claim 3 wherein the tip of the lance is provided with a pair of divergent nozzles to produce an outwardly fanning jet having an included angle in the range of 16° to 47°.

7. An electric arc furnace comprising a vessel for holding molten metal;

heating means operable to heat molten metal within the vessel including at least one electrode placed within the vessel;

and at least one oxygen lance operable to direct a jet of oxygen downwardly into the molten metal in the vessel in a general direction which is inclined downwardly by an angle in the range of 35° to 50° from the horizontal and which diverges away from a direct line to a central region of the vessel through a horizontal divergence angle in the range of 10° to 50°, and wherein said horizontal divergence angle is in the range of 30° to 35°.

8. An electric arc furnace according to claim 7, wherein said horizontal divergence angle is 31.5°.

9. An electric arc furnace according to claim 3 wherein said inclined angle is in the range of 38° to 47°.

10. An electric arc furnace according to claim 3 wherein the vessel has a hearth shape which comprises a crucible at one end and a balcony at the other end with the crucible providing a deeper reservoir for the molten metal than the balcony.

11. An electric arc furnace according to claim 10 wherein the balcony is provided with any one of a taphole in its bottom and an outwardly projecting spout in its wall.

12. An electric arc furnace according to claim 10 wherein the balcony extends from one side of the crucible thereby forming a hearth having an upper portion of any one of tear-drop, elliptical or ovoid shape in horizontal cross-section.

13. An electric arc furnace according to claim 12 wherein the vessel is adapted to hold ferrous materials for melting and refining into said molten metal and the heating means consists of three electrodes to facilitate melting of said ferrous materials.

14. A method of heating molten metal within a vessel comprising a hearth having a crucible and a balcony, in which the balcony extends from one side of the crucible thereby forming a hearth having an upper portion of any one of tear-drop, elliptical or ovoid shape in horizontal cross-section and the crucible is of generally cup shape and provides a deeper reservoir for the molten metal than the balcony and which includes the step of directing a jet of oxygen downwardly into the molten metal in the vessel in a general direction which is inclined downwardly by an angle in the range of 35° to 50° from the horizontal and which diverges away from a direct line to a central region of the vessel by a horizontal divergence angle in the range of 10° to 50°.

15. A method according to claim 14 wherein said horizontal divergence angle is in the range of 30° to 35°.

16. A method according to claim 14 wherein said horizontal divergence angle is 31.5°.

17. A method according to claim 14 wherein said inclined angle is in the range of 38° to 47°.

18. A method according to claim 14 wherein the method further comprises the steps of placing materials into the vessel and melting and refining the materials to provide said molten metal.

19. A method according to claim 14 wherein the method comprises the further step of heating the molten metal to a predetermined temperature prior to tapping.

20. A method according to claim 19 wherein the melting and heating steps are provided by electric arc heating.

21. A method according to claim 20 wherein the electric arc heating is provided by three electrodes within the vessel.

22. A method according to claim 14 wherein the vessel is a hearth of an electric arc furnace having a crucible and a balcony and the crucible is adapted to hold ferrous material for melting and refining into said molten metal and three electrodes facilitate melting of said ferrous material and heating of the molten metal.

23. A method according to claim 22 comprising the further step of tapping molten metal through a taphole provided in the bottom of the balcony and that tapping is facilitated by tilting of the vessel.

24. A method according to claim 23 wherein the vessel is so shaped to enable some molten metal to remain in the crucible at the conclusion of the tilting/tapping operation to prevent slag entrainment when tapping the steel.

25. A method according to claim 14 wherein the step of directing a jet of combustible gas is provided by the use of a water cooled oxygen lance.

26. A method according to claim 25 wherein the lance is provided with a tip and the tip of the lance is disposed above the molten metal.

27. A method according to claim 26 wherein further the tip is provided with a pair of divergent nozzles having an acute included angle of about 30°.

28. A method according to claim 27 wherein the lance is mounted on a stand at the crucible end of a vessel in the form of a hearth having a balcony end and a crucible end.

29. A method according to claim 14 wherein the method comprises the further step of providing a gas injection port in the crucible bottom proximal to the balcony of the vessel.

* * * * *